United States Patent [19]

McDaniel

[11] Patent Number: 4,925,477

[45] Date of Patent: May 15, 1990

[54] CHEMICAL HYBRIDIZING AGENTS

[75] Inventor: Robert G. McDaniel, Tuscon, Ariz.

[73] Assignee: Research Corporation, New York, N.Y.

[21] Appl. No.: 902,289

[22] Filed: Aug. 29, 1986

[51] Int. Cl.$^5$ ............................................. A01N 43/60
[52] U.S. Cl. ........................................ 71/77; 71/86; 71/92; 71/103; 71/128
[58] Field of Search ...................... 71/128, 92; 514/249

[56] References Cited

PUBLICATIONS

Langhals, H. et al., "Easy Transformation of Benzylic Alcohols, etc.", CA 86, 72120n, (1977).
Boveris, A. et al., "Chemiluminescence of Soybean Seeds: etc.", CA 99, 155535w, (1983).
Van Paasschen, J. M. et al., "Preparation of the Piperazine-etc.", CA 83, 21210x, (1975).
McDivitt, R., "Spectral Studies of 1,4-diazabicyclo 2.2.2 octane, etc.", Diss. Abst. Int. B, 1971, 31(8), 4617.

Primary Examiner—Richard L. Raymond
Assistant Examiner—Amelia A. Owens
Attorney, Agent, or Firm—Scully, Scott, Murphy & Presser

[57] ABSTRACT

The present invention relates to a method for inducing male sterility in plants which comprises treating seeds of a plant receptive to said treatment by application of an effective amount of a compound of the formula:

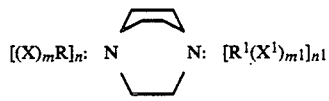

wherein

R and $R^1$ are hydrogen, alkyl, alkenl, alkynl, allyl, aryl, halogen or boron and may be the same or different;

X and $X^1$ are fluorine, chlorine, bromine or iodine; nitrate, sulfate, sulfonate, phosphate, citrate, or maleate;

n and $n^1$ are the integers 0 or 1, and may be the same or different;

m and $m^1$ are integers from 0 to 4, and may be the same or different;

for a period of time and under conditions sufficient to induce male sterility in adult plants which are grown from said treated seeds.

6 Claims, No Drawings

CHEMICAL HYBRIDIZING AGENTS

FIELD OF THE INVENTION

The present invention relates to chemical hybridizing agents; more specifically it relates to the use of these agents in inducing male sterility in plants.

BACKGROUND OF THE INVENTION

Plant breeders have long been attempting to increase productivity of the more important crops used for food, or for processing as feed, fiber and pharmaceuticals, by their efforts in developing cultivars (cultivated varieties) with particularly desirable characteristics. One of the ways in which this aim is frequently accomplished is the development of superior plant lines by infusing desirable traits with already existing cultivars, thus potentially forming a hybrid with exceptional characteristics. The general superiority of $F_1$ hybrids over either of their parents is a widespread phenomenon in a variety of different types of crops. This superiority may express itself in such features as increased height, growth rate, leaf area, early flowering and overall higher yields.

One way in which the production of superior plant lines has been achieved in the past is by the making of numerous manual cross pollinations to obtain the desired $F_1$ hybrid. These crosses generally are carried out between an already existing cultivated crop variety and an unadapted or "wild type" gene donor which possesses one or more traits which the breeder wishes to incorporate into the cultivated variety. Once the production of the $F_1$ has been accomplished, repeated backcrossings and selections are then required to ultimately obtain a plant containing all the characteristics of the cultivated plant as well as retaining the new, desirable traits introduced from the "wild type" plants. As can easily be seen, this selection procedure is extremely tedious and time consuming; yet, in spite of the difficulties, it remains one of the most widespread of plant breeding techniques currently in use.

Because of the problems involved with this method, a number of other avenues for more efficient production of $F_1$ hybrids have been and are being explored. Among the most avidly pursued fields of endeavor is the construction of male sterile lines within the varieties of crop plants to which hybridization is desired. The principle behind the development of male sterile lines is that, in order to produce hybrid seed more economically, the restrictions of controlled cross-fertilization imposed by floral morphology, especially of perfect flowers, must be overcome. To this end, the female parent should be prevented from self- or intraline fertilization. The elimination of self-fertilization requires andro-self sterility, or the inability of the plant to produce viable pollen. The establishment of the male sterile line then renders any crop variety readily adaptable to hybridization with virtually any gene donor having the desired characteristics, and eliminates the need for laborious hand pollination.

Male sterile lines may be established in a number of ways. Hand emasculation is one method by which a line may be sterilized. For example, large scale production of hybrid corn may be done by detasselling the female parent; however, the large scale emasculation of species having perfect flowers generally proves to be economically unfeasible.

Genetic male sterility is also a known trait, usually inherited as a recessive and monogenic trait in a number of different types of plants. Exploitation of this characteristic is used to produce hybrid seed of barley, tomato, pepper, marigold, zinnia, and others. However, there is a basic shortcoming in the use of this technique, in that it is difficult to obtain a 100% genetic male sterile stand. Overcoming this difficulty requires a rather complex use of clever genetic manipulation. Its use, therefore is currently restricted to hybrid seed production of cultivated plants in which cytoplasmic male sterility has not been found, or that in which the male sterile plasmatype exhibits inferior agronomic performance.

Cytoplasmic male sterility provides an additional mechanism for providing the desired lines for use in hybridization. In this situation, the genetic factors controlling male sterility are found in the cytoplasm. This trait is probably associated with some alteration of the normal structure or function of mitochondria of plastids. Cytoplasmic male sterility has found widespread application in the production of hybrid seed. Widespread production based on this trait is responsible for larger percentages of many important cultivated crops such as sorghum, sugarbeet, onions, melon, and, most successfully, corn. A number of difficulties exist with this system as well. First, it is difficult to ensure the expression of cytoplasmic male sterility across the range of environments in which hybrid seed may be produced. A female wheat plant which is 100% sterile in one locality may prove to be only 50% sterile in another locality, thus producing obvious difficulties in hybrid seed production.

Furthermore, once the sterile line is established, the female line must be maintained through the use of a male fertile maintainer line; and hybrid seed must be restored to at least semi-sterility via a "restorer" line. Clearly the necessary development of effective and appropriate maintainer and restorer lines presents a considerable obstacle to the efficient and economical exploitation of the trait for the production of hybrid seed. In fact, a number of important cereal crops, such as wheat, have continued to resist all efforts to establish efficient cytoplasmic male sterility restorer lines.

A method of producing male sterile lines which circumvents the difficulties of genetic induction is the use of chemical sterilization agents. The principle involved here is that the chemical acts as a gametocide selectively altering the male gamete, i.e., pollen, by inducing physiological abnormalities, which in turn prevent pollen development, pollen shed, or pollen viability. A number of chemical compounds have been shown to have at least a partial effect in producing male sterility in plants. Among these are: 2-chloroethylphosphonic acid (ethephon; Berhe et al., *Crop Science* 18: 35–38, 1978); sodium 1-(p-chlorophenyl)-1,2-dihydro-4,6-dimethyl-2-oxonicotinate (RH-531+532; Jan et al., *Euphytica* 23: 78–85, 1974); 3-(p-chlorophenyl)-6-methoxy-s-triazine-2,4 (1H,3H) dione-triethanolamine (DPX3778; Johnson et al., *Crop Science* 18: 1026–1028; 2,7-diamino-10-ethyl-6-phenylantridium bromide (ethidium bromide; Burton et al., *Crop Science* 16: 731–2, 1976). Although use of these compounds obviate the problems encountered with genetic manipulation, there are still a number of difficulties which might arise with use of chemisterilants. For example, chemical treatment may result in induction of only partial sterility, or may be variable in the degree of male sterility induced under field conditions. They also may produce phytotoxic side effects, such as seed shrinking, which may reduce the viability and/or agricultural utility. Further, female sterility may also be induced by the use of some of these chemicals. Another undesirable feature is that for the most part, these compounds are applied as foliar sprays. The necessity of such application presents the problem of environmental pollution, and synchrony with the exact plant stage of development.

It has now been discovered that another class of compounds, DABCO (1,4-Diazabicyclo[2.2.2]octane) and its quaternary salt derivatives have the unexpected effect of causing male sterility in plants. The subject compounds, which are preferably used to treat seeds directly, are thus not limited to use as foliar chemisterilant sprays, although this is an alternate method of application. Use of these compounds for chemical emasculation allows for the development of all female plants which may be used to produce large quantities of hybrid seed. These compounds have the added advantage of producing male sterility in wheat, a plant which has traditionally resisted all attempts to establish a successful hybrid seed production program.

BRIEF DESCRIPTION OF THE INVENTION

The present invention relates to a method of inducing substantial male sterility in plants which comprises applying to seeds of said plants receptive to such induction an effective amount of compounds of the formula:

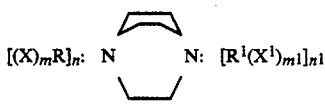

wherein
R and $R^1$ are hydrogen, alkyl, alkenyl, alkynyl, allyl, aryl, halogen or boron and may be the same or different;
X and $X^1$ are fluorine, chlorine, bromine; iodine; nitrate, sulfate, sulfonate, phosphate, citrate, or maleate;
n and $n^1$ are the integers 0 or 1, and may be the same or different;
m and $m^1$ are integers from 0 to 4;
for a period of time and under conditions sufficient to induce male sterility in adult plants which develop from said treated seeds.

Also provided by the present invention is a composition of matter useful for inducing male sterility in plants, which comprises an effective amount of the above compounds in combination with a carrier solvent.

It is preferred that the alkyl, alkenyl and alkynyl groups have no more than 6 carbon atoms and that the aryl group be either benzyl or phenyl.

It also provides a method for the production of hybrid seed by cross-breeding male and female parents of different genotype, the improvement comprising utilizing as the female parent a plant grown from seed treated with an effective amount of DABCO or one of the DABCO-halogen derivative.

DETAILED DESCRIPTION OF THE INVENTION

The active compounds of the present invention are primarily quaternary salts of the compound 1,4-diazabicyclo (2.2.2) octane (DABCO). DABCO is a known compound, as are some of its halogen derivatives (see U.S. Pat. No. 3,150,136, the disclosure of which is incorporated herein by reference). Some of the known uses for DABCO compounds are as antibacterial agents, or for ganglionic blocking and as a central nervous system depressant. It has heretofore not been known to use DABCO or its quaternary salts in the process of inducing male sterility in plants, however. The useful salts of the present invention may be mono- or-di-quaternary salts of DABCO. Particularly preferred are the halogen derivatives of DABCO, and most preferred are DABCO-benzyl chloride, and DABCO-$BCl_3$. The DABCO compound itself is also contemplated for use in the present method.

The present process of male sterility induction is implemented by the treatment of seeds of a plant possessing characteristics which are deemed desirable for the specific purpose, with DABCO or one of its quaternary salts as noted above. The treatment serves, in a manner which is not yet certain, to prevent pollen formation in the adult plant which is ultimately derived from a treated seed. Thus is provided a stand of plants which is functionally all female, and which can then be selectively hybridized by pollination by a plant having different features which may be desirable to incorporate into the genome of the male sterilized plant. The resulting hybrid seed contains the superior traits of both the all-female plants and the selected plant by which it was pollinated. Therefore, the resulting seeds would produce adult plants which are superior to both parent plants in that the desirable traits of each are combined into a single plant. The present process is particularly well-suited for plants which are generally self-fertilizing, such as wheat.

The treatment of the seeds is a relatively simple process. The DABCO salts are generally dissolved in a hydrocarbon carrier solvent, such as carbon tetrachloride or benzene, DMSO, or water. Particularly preferred as a solvent is DMSO (dimethylsulfoxide) at a concentration of 0.2-20% preferably about 5%. DMSO is preferred because of its independent effect of inducing some level of male sterility. The active ingredient is added to the carrier to produce a final concentration within the range of 0.01-100 millimolar, with the preferred concentration being about 1 mM. The remaining volume of the solution is made up with double distilled water. The seeds to be used may be surface sterilized prior to their treatment with the chemisterilant. The seeds may be placed in any suitable container, such as a petri dish, and the active chemical solution added. As the present compounds tend to deteriorate with time, and may yield unpredictable or unwanted results when left for long periods of time, it is generally preferred to use relatively fresh preparations. In some cases, depending upon the thickness of the seed coat, it is desirable to scarify the seeds to expedite entry of the treatment solution before germination. The amounts needed for treatment may vary, but generally 2 ml/20 seeds is sufficient to produce the desired result. The seeds may then be covered and incubated in a growth chamber for a period of at least 24 hours. The seeds may then be placed in soil and maintained in a manner consistent with the usual growing conditions for the plant in question. The plants are allowed to mature, and pollination procedures of various types well-known in the field may be employed upon ripening of the female plant, to produce the desired hybrid seed.

The treatment prescribed herein may be applied to a wide variety of seed types, although, to date, best results have been observed with monocot seeds. The present method has been particularly successful with wheat seeds. However, the process is, in principle, applicable to any type of plant seed. Whether the present method is useful in producing male sterility in any given seed type may be readily determined by following the above-outlined procedure. After the treated seeds have been planted and grown to maturity, it is a relatively simple matter, particularly in self-fertilizing plants, to observe the seed set of the plants derived from the treated seeds. Absence or reduction of seed set indicates the effectiveness of inducing sterility by the treatment. Certain modifications of the abovementioned protocol may be required to obtain completely satisfactory results. For example, concentration of the active ingredient, or length of incubation may have to be varied depending upon the type of seed used. It is, however, easily within the ability of one skilled in the art to determine the appropriate adjustments which will render the treatment most effective.

Many of the compounds to be used in connection with the present invention are, as noted above, previously known. They may generally be prepared according by first making the parent molecule, DABCO, anhydrous. This is achieved by sublimation under reduced pressure, in the presence of a solvent such as dry benzene, dry carbon tetrachloride or other dry carbon tetrachloride or other hydrocarbons. The appropriate halide, e.g., boron trichloride or boron trifluoride, is then added dropwise to the DABCO in an appropriate solvent with stirring, under nitrogen. Complexes generally form within an hour, but reaction time will depend to some extent on the temperature and the halide used. The solid DABCO-halogen complexes are removed by filtration and washed with ethyl ether to remove unreacted DABCO and excess carbon tetrachloride, and further washed with distilled water, if necessary, to remove amine salts. After drying in a vacuum oven, the complexes are stored, in the dark, at 80° F. or less.

Although the mechanism of action of these compounds is not, at the present time, determinable with any certainty, it appears probable that these chemicals act to alter DNA synthesis, particularly mitochondrial DNA synthesis, in such a manner that the genes which condition male fertility are either rendered non-functional, are preferentially under-replicated, or are preferentially cut out of the DNA and lost. This apparent ability to act as DNA intercalators may indicate a potential utility for the compounds as genetic engineering tools.

The advantages of the use of the present compounds over previously known chemical sterilizing agents are many. First, they may be applied directly to the seeds, rather than as a foliar spray to adult plants. This avoids both the problems of environmental pollution, and the necessity of synchrony with the exact stage of plant development. They have also proven useful in producing male sterility in wheat, a plant which has traditionally resisted efforts to establish male sterile lines. Also, the compounds appear to have little or no effect on female fertility in plants grown from treated seeds. The present invention will become more clearly understood by reference to the following non-limiting examples.

EXAMPLE 1

This example illustrates the process of preparing DABCO-boron trichloride.

To a solution of 50 grams of Anhydrous DABCO (Houdry Process and Chemical Co., Philadelphia) in 500 ml of carbon tetrachloride, is added 117 grams of boron trichloride dropwise with stirring under a dry nitrogen atmosphere. At 30° the reaction is complete within about 1.5 hours., and the solid boron trichloride may be removed by filtering. The resulting solid white complex, is then washed with ethyl ether to remove unreacted DABCO and excess carbon tetrachloride, then with water to remove amine salts. The complex is dried at 110° in a vacuum oven, and subsequently stored in the dark.

Employing analogous procedures, the following compounds have also been made.

| | Dabco + HF + HCl | | Dabco + 2CH$_2$Br$_2$ |
|---|---|---|---|
| Dabco + HF | Dabco + HCl + HI | Dabco + 2Br$_2$ | Dabco + CH$_2$BrCl |
| Dabco + 2HF | Dabco + HBr + HI | Dabco + I$_2$ | Dabco + CBr$_4$ |
| Dabco + 2HCl | Dabco + CH$_3$Cl | Dabco + 2IBr | Dabco + benzylchloride |
| Dabco + 2HBr | Dabco + CH$_2$Cl$_2$ | Dabco + 2BCl$_3$ | Dabco + 1-brom-2-methyl propane |
| Dabco + 2HI | Dabco + CH$_2$Br$_2$ | Dabco + allyl bromide | |
| Dabco + HBR + HF | | | |

EXAMPLE 2

The following example illustrates the typical experimental procedure used for treating seeds with the compounds of the present invention:

Test chemicals were made to 1.0 millimolar concentration in 5% distilled dimethyl sulfoxide in a total volume of 2 ml. double-distilled water. The control was 5% DMSO solution. Sets of twenty surface-sterilized wheat seeds (*Triticum durum* L. cv. 'Jori') were placed in a falcon plastic petri dish on a double layer of Whatman No. 2 filter paper. Two ml. of DABCO-BCL$_3$ was added to each petri dish. The solution beaker was rinsed with 1.0 ml deionized water, and the washing poured over a third filter paper disc covering the seed. The petri dishes were covered, incubated in a lighted growth chamber for 24 hr., and then placed in plastic pots containing a standard potting soil mix. Each of the groups of 20 treated seeds were randomly distributed to five pots, four seeds per pot; and the pots were placed randomly on the greenhouse bench. Plants were grown to maturity in a greenhouse, with occasional supplemental watering with nutrient solution, and with one chemical treatment for insect control. Seeds were allowed to mature, ripen and dry down in the heads prior to harvest.

The results of a typical experiment are outlined in Table 1. No difference in time of development, leaf morphology, viability, or plant height were noted in any treatment, as compared with the control. Tests were also performed to determine the effect of Dabco-boron trichloride on female fertility. The results presented in Table 1a suggest that female fertility is not substantially affected by the treatment with Dabco-halogen complexes.

TABLE 1

Effect of DABCO-boron trichloride on reproductive properties of greenhouse-grown "Jori" wheat.

| Treatment | Number of seeds/ plant | Length of rachis (cm) | Number of sterile spikelet groups/head | Number of rachis nodes/head |
|---|---|---|---|---|
| Control (5% DMSO) | 15.7 a | 3.19 a | 0.43 a | 10.3 a |
| Dabco-boron trichloride (1 mM) | 9.9 b | 3.70 a | 2.36 b | 9.7 a |

Means in columns not followed by the same letter are significantly different at the 5% level.

TABLE 1a

Effect of DABCO-boron trichloride on female fertility of greenhouse-grown "Jori" wheat.

| Treatment | Number of seed/ plant | Weight of seed/ plant (g) | Number of spikelet groups/plant | Plant Height (cm) |
|---|---|---|---|---|
| Control (DMSO) (4 plants) | 26.8 | 1.2 | 14.8 | 53.3 |
| DABCO-boron trichloride (3 mM) (4 plants) | 34.8 | 1.4 | 15.8 | 56.5 |
| DABCO-boron trichloride (1 mM) (3 plants) | 19.0 | 0.9 | 13.0 | 54.2 |

Pollen from selected untreated plants was used to cross-fertilize receptive ovules in heads of DABCO-complex treated plants the day following clipping of the tops of the lemma and palea to facilitate cross pollination.

EXAMPLE 3

The preceding protocol was followed in an additional experiment in which ethidium bromide and adriamycin were compared with DABCO-BCl₃ for effectiveness in reducing seed set. The results are presented in Table 2. Although both comparison compounds had a noticeable effect on reduction of seed numbers, only DABCO-BCl₃ showed a statistically significant reduction in seed number.

TABLE 2

Effect of chemical seed treatments on seed set and spike characteristics of uniculum wheat.

| Treatment | Number of seeds/ head | Weight of seeds/ head (cm) | Number of sterile spikelet groups/head | Number of rachis nodes/ head |
|---|---|---|---|---|
| Control (5% DMSO) | 28.8 b | 1.44 b | 0.95 b | 15.9 a |
| Dabco-BCl₃ | 16.3 a | 0.96 a | 3.50 a | 16.4 a |
| Ethidium Bromide | 27.1 b | 1.46 b | 1.00 b | 16.8 a |
| Adriamycin | 26.5 b | 1.49 b | 0.37 b | 16.7 a |

Means in columns not followed by the same letter are significantly different at the 5% level judged by both Duncan's New Multiple Range Test and Student Neumann-Keuls procedure. All treatments applied in 5% DMSO.

EXAMPLE 4

The procedure of Example 2 was followed for treatment of barley seeds. The results are summarized in Table 3.

TABLE 3

Effect of Dabco-boron trichloride on reproductive properties of field-grown "Gus" barley

| Treatment | Number of seeds/ plant | Number of sterile spikelet groups/plant | Number of spikelet groups/ plant | Plant Height (cm) |
|---|---|---|---|---|
| Control (10 plants) (deionized H₂O) | 32.8 | 0.5 | 13.1 | 31.5 |
| DABCO-boron trichloride (1 mM) (9 plants) | 19.8 | 2.7 | 11.3 | 29.3 |

Seeds were soaked twice as long as those in Table 1.

What is claimed is:

1. A method of inducing male sterility in plants which comprises treating seeds of a monocot plant receptive to said treatment by application of an effective amount of a compound of the formula:

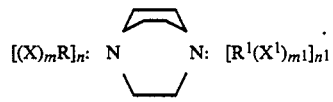

wherein

R and R¹ are hydrogen, alkyl, alkenyl, alkynyl, benzyl, phenyl, halogen or boron and may be the same or different and said alkyl, alkenyl and alkynyl have no more than six carbon atoms;

X and X¹ are fluorine, chlorine, bromine or iodine; nitrate, sulfate, sulfonate, phosphate, citrate, or maleate;

n and n¹ are the integers 0 or 1, and may be the same or different;

m and m¹ are integers from 0 to 4, and may be the same or different;

for a period of time and under conditions sufficient to induce male sterility in adult plants which develop from said treated seeds.

2. The method of claim 1 wherein the plant is wheat.

3. The method of claim 1 wherein the compound is DABCO-BCl₃.

4. The method of claim 1 wherein the compound is DABCO-benzyl chloride.

5. A selective male sterilant composition useful in induction of male sterility in plants which comprises an effective amount of at least one compound of the formula:

in combination with DMSO as a carrier solvent, wherein R and R¹ are hydrogen, alkyl, alkenyl, alkynyl, benzyl, phenyl, halogen or boron and may be the same or different and said alkyl, alkenyl and alkynyl have no more than six carbon atoms;

X and X¹ are fluorine, chlorine, bromine or iodine; nitrate, sulfate, sulfonate, phosphate, citrate, or maleate;

n and n¹ are the integers 0 or 1, and may be the same of different;

m and m¹ are integers from 0 to 4 and may be the same of different.

6. A method of inducing male sterility in plants which comprises treating a plant physiologically committed to flowering by foliar application of an effective amount of a compound of the formula:

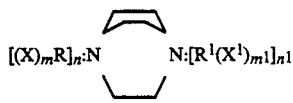

wherein
R and $R^1$ are hydrogen, alkyl, alkenyl, alkynyl, benzyl, phenyl, halogen or boron and may be the same or different and said alkyl, alkenyl and alkynyl have no more than six carbon atoms;

X and $X^1$ are fluorine, chlorine, bromine or iodine; nitrate, sulfate, sulfonate, phosphate, citrate, or maleate;

n and $n^1$ are the integers 0 or 1, and may be the same or different;

m and $m^1$ are integers from 0 to 4, and may be the same or different;

for a period of time and under conditions sufficient to induce male sterility in adult plants which develop from said treated plants.

* * * * *

UNITED STATES PATENT AND TRADEMARK OFFICE
CERTIFICATE OF CORRECTION

PATENT NO. : 4,925,477
DATED : May 15, 1990
INVENTOR(S) : Robert G. McDaniel

It is certified that error appears in the above-identified patent and that said Letters Patent is hereby corrected as shown below:

Column 4, line 54: "amounts" should read as --amount--

Signed and Sealed this

First Day of October, 1991

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,925,477
DATED : May 15, 1990
INVENTOR(S) : Robert G. McDaniel

It is certified that error appears in the above-identified patent and that said Letters Patent is hereby corrected as shown below:

Column 3, line 66: "3,150,136" should read as --3,150,138--.

Signed and Sealed this

Thirty-first Day of December, 1991

Attest:

HARRY F. MANBECK, JR.

Attesting Officer

Commissioner of Patents and Trademarks